US005635346A

United States Patent [19]

Leahy et al.

[11] Patent Number: 5,635,346
[45] Date of Patent: Jun. 3, 1997

[54] ASSAY FOR NON-A NON-B HEPATITIS

[75] Inventors: David C. Leahy, Arlington Hts.; John A. Todd, Grayslake; Michael E. Jolley, Round Lake; Dinesh O. Shah, Vernon Hills; Delia R. Bethell, Wilmette, all of Ill.; Terukatsu Arima, Kagoshima, Japan

[73] Assignee: Dade International Inc., Deerfield, Ill.

[21] Appl. No.: 372,723

[22] Filed: Jan. 17, 1995

Related U.S. Application Data

[63] Continuation of Ser. No. 108,778, Aug. 18, 1993, abandoned, which is a continuation of Ser. No. 675,233, Mar. 26, 1991, abandoned.

[51] Int. Cl.⁶ .................. C12Q 1/70; C07K 14/18
[52] U.S. Cl. .................. 435/5; 435/7.1; 435/7.92; 530/324
[58] Field of Search .................. 435/5, 7.1, 7.92; 530/324, 326

[56] References Cited

FOREIGN PATENT DOCUMENTS

| 0190972 | 8/1986 | European Pat. Off. . |
| 0318216 | 5/1989 | European Pat. Off. . |
| 0363025 | 4/1990 | European Pat. Off. . |
| 0388232 | 9/1990 | European Pat. Off. . |
| 2212511 | 7/1989 | United Kingdom . |
| 9000597 | 1/1990 | WIPO . |
| 9002206 | 3/1990 | WIPO . |

OTHER PUBLICATIONS

Bradley, et al., *J. Infect. Dis.*, 148:254 (1983).
Hotta & Evans, *Virology* 2:705–706 (1956).
Davis, *PNAS*, 80:1194 (1983).
Cabral et al., *Gastroent.*, 81:120 (1981).
Tobin et al., *Proc. Nat. Acad. Sci* 76:4350 (1979).
Walsh et al., *J. Infect Dis.* 21:550 (1970).
Diamandis, *Clin. Biochem.*, 21:139 (1988).
Crook et al., *J. Gen. Virol.*, 46:29 (1980).
Tojo et al., *Clin. Chem.*, 34:2423 (1988).
Jahn et al., *Proc. Natl. Acad. Sci*, 81:1684 (1984).
Jolley et al., *J. Immunol. Meth.*, 67:21 (1984).
Kuo et al. Science, vol. 244, Apr. 1989, pp. 362–364.
Roitt "Essential Immunology" 4th Ed., 1980, Blackwell Scientific Publications, pp. 144–149.

*Primary Examiner*—David Guzo
*Attorney, Agent, or Firm*—Cynthia G. Tymeson

[57] ABSTRACT

New assays for diagnosing NANBH utilizing novel peptide fragments derived from polypeptide antigens reactive to antibodies present in the sera of infected patients are disclosed. In producing these peptides, the portion of the polypeptide contributing to high backgrounds is deleted thereby resulting in assays with an exceptionally high signal to background ratio.

7 Claims, 2 Drawing Sheets

FIG. 1

| Sequence | Range | Peptide Designation |
|---|---|---|
| FQEKKGEASNGEAENDTHKKQRRYKEKEKTATNNPGKNKKPRVGRIKNWNREGRKDAYQIRKRR | 1–63 | A |
| QEKKGEASNGEAENDTHKKQRRYKEKEKTATNNPGKNKKPRVGRIKNWNREGRKDAYQIRKRR | 12–63 | B |
| QEKKGEASNGEAENDTHKKQRRYKEKEKTATNNPGKNKKPRVGRIKNWNREGRKDAYQIRKRR | 21–63 | C |
| QEKKGEASNGEAENDTHKKQRRYKEKEKTATNNPGKNKKPRVGRIKNWNREGRKDAYQIRKRR | 36–63 | D |
| QEKKGEASNGEAENDTHKKQRRYKEKEKTATNNPGKNKKPRVGRIKNWNREGRKDAYQIRKRR | 12–35 | E |
| QEKKGEASNGEAENDTHKKQRRYKEKEKTATNNPGKNKKPRVGRIKNWNREGRKDAYQIRKRR | 9–30 | F |
| QEKKGEASNGEAENDTHKKQRRYKEKEKTATNNPGKNKKPRVGRIKNWNREGRKDAYQIRKRR | 28–43 | G |
| QEKKGEASNGEAENDTHKKQRRYKEKEKTATNNPGKNKKPRVGRIKNWNREGRKDAYQIRKRR | 23–63 | H |
| QEKKGEASNGEAENDTHKKQRRYKEKEKTATNNPGKNKKPRVGRIKNWNREGRKDAYQIRKRR | 24–63 | I |
| QEKKGEASNGEAENDTHKKQRRYKEKEKTATNNPGKNKKPRVGRIKNWNREGRKDAYQIRKRR | 26–63 | J |
| QEKKGEASNGEAENDTHKKQRRYKEKEKTATNNPGKNKKPRVGRIKNWNREGRKDAYQIRKRR | 29–63 | K |
| QEKKGEASNGEAENDTHKKQRRYKEKEKTATNNPGKNKKPRVGRIKNWNREGRKDAYQIRKRR | 31–63 | L |
| QEKKGEASNGEAENDTHKKQRRYKEKEKTATNNPGKNKKPRVGRIKNWNREGRKDAYQIRKRR | 9–45 | M |
| QEKKGEASNGEAENDTHKKQRRYKEKEKTATNNPGKNKKPRVGRIKNWNREGRKDAYQIRKRR | 23–56 | N |

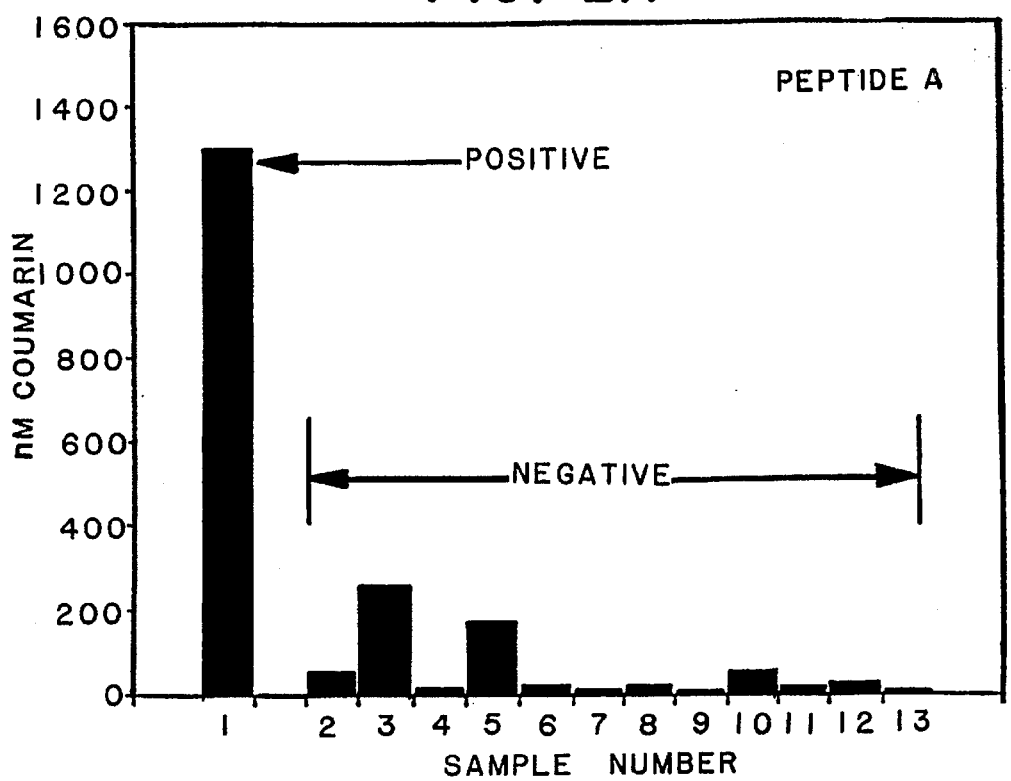
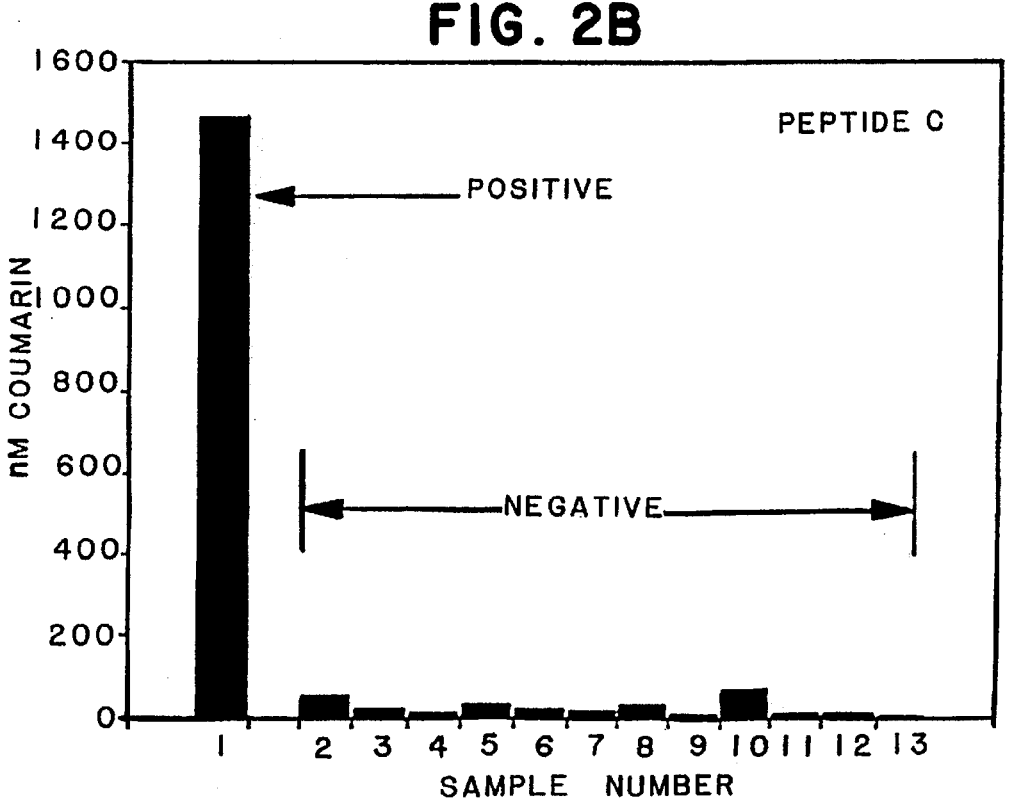

ASSAY FOR NON-A NON-B HEPATITIS

This is a continuation, of application Ser. No. 08/108,778, filed on Aug. 18, 1993, abandoned, which is a continuation of Ser. No. 07/675,233, filed Mar. 26, 1991, abandoned.

BACKGROUND OF THE INVENTION

The discovery of the causative agent of hepatitis B together with the development of highly sensitive assays for the detection of the agent in donated blood, led to rapid virtual elimination of this virus from the blood supply. However other viral forms of transfusion-associated hepatitis soon became apparent, and have been termed generally Non-A Non-B hepatitis (NANBH). It is apparent from studies involving passaging of infected blood in chimpanzees that there exists more than one species of infective agent causative of NANBH (For example, see Bradley, et al., J. Infect. Dis., 148: 254 (1983)). It is also apparent from the early studies that isolation of pure virus would be extremely difficult because its presence in blood, even in the acute phases of infection, is on the order of only 1000 infective units per ml.

In spite of the failure of primary isolation, the virus was nevertheless characterized preliminarily by a number of criteria. Inactivation of the agent by chloroform implicated an envelope virus (Hotta & Evans, Virology, 2: 773 (1985)). Filtration of NANBH agents through membranes of different pore size indicated a size range of 30–60 nm. It was further determined that NANBH agents sedimented at approximately 200 S with a buoyant density of 1.24 g/cc. Finally, the agent was visualized by electron microscopy (Cabral, et al., Gastroent., 81: 120 (1981). All of the data are consistent with the conclusion that NANBH agents are toga or flaviviruses, or members of a group closely related to the toga or flaviviruses.

The breakthrough in NANBH research came in the course of passaging the NANBH virus, obtained from a contaminated purified Factor VIII, through chimpanzees. Bradley, et al., Seminars in Liver Disease, 6: 56 (1986) discovered that the titer of NANBH infective units in one particular chimpanzee was a thousand fold greater than the titer ordinarily observed. This enriched source of NANBH agent permitted the creation and screening of a cDNA library by Houghton, et al (EP 0 318 216) utilizing the lambda gtll system devised by Young & Davis, PNAS, 80: 1194 (1983). EP 0 318 216 discloses a large open reading frame domain, which includes the C-100 polypeptide which is the target antigen in a commercial immunoassay for diagnosis of NANBH. This disclosure is supplemented in a second European Patent Application (EP 0 388 232) which discloses further sequences representing a sizable portion of the polypeptide possibly corresponding to the 5 prime end of the viral genome encoding putative structural proteins.

Other recent foreign applications include WO 90,02206 (Seto) which discloses further sequences cloned from liver sections of patients suffering from NANBH. WO 90/00597 (Neeley) presents a method of producing virus from immortalized human liver cells productive of active NANBH virus. An alternative method for preparing viral antigen is disclosed in EP 0 190 972 (Yohko) and involves a centrifugation procedure on sucrose gradients of proteins derived from infected chimpanzee liver tissue. Monoclonal antibodies were also obtained in '972 by transforming lymphocytes from NANBH infected humans or chimpanzees with Epstein-Barr virus, and screening for clones secreting antibody specific for the gradient purified antigens. The above NANBH polypeptide sequences are said to be useful in diagnostic assays.

Additional sequences for NANBH are set forth in EP 0 363 025 (Arima). The sequences were obtained from RNA extracted from viruses concentrated from approximately 100 liters of plasma from patients with NANBH. Sequences were identified by immunoscreening of a lambda gtll cDNA library. Of those clones screening positive, one such clone contained the clone 18 peptide having the amino acid sequence described in claim 2 formulae III in EP 0 363025 (Arima).

SUMMARY OF THE INVENTION

In formatting an assay for detection of antibodies contained in patient sera to a NANBH agent, a polypeptide of 63 amino acids having the amino acid sequence QEKKGEASNGEAENDTHKKQRRYKEKEKTATNNPGKNKKPRVGRIKNWNREG RKDAYQIRKRR, SEQ ID NO:1, known to be immunoreactive with certain NANBH sera as described by Arima in EP 0 363 025, was modified by progressively shortening the sequence from the amino terminal end of the molecule. The improved assay of the present invention utilizes a shortened fragment substantially homologous to the portion of the polypeptide extending sequentially from an amino acid residue selected from the group consisting of amino acids contained within the sequence from residue 21 to 26 to substantially the carboxy-terminal arginine.

In another aspect of the present invention, the peptide fragment contains at least one epitope reactive to sera (obtained from individuals afflicted with NANBH), but deletes the portion of the 63 amino acid polypeptide extending from any of the amino acids of residues 21 to 26 to the N-terminus, which has been found to contribute to non-specific binding, high background and false positive signal in immunoassays. These peptides have utility both as vaccines and in diagnostic or screening assays.

In one embodiment of the improved assay utilizing the peptides of the present invention, a target peptide fragment is coated onto a solid matrix, and the assay is carried out by incubating with a sample containing antibodies directed to the peptide forming an antibody peptide complex, separating unreacted sample from the complex immobilized onto the said solid matrix, and quantitating the amount of antibody in the complex by detection means.

In another embodiment of the improved assay, the target fragment is conjugated to a fluorophore, and the assay is carried out by incubating it with a sample containing antibodies to the peptide to form an antibody peptide complex, and measuring the fluorescence polarization of the complex in solution. Thus, by such homogeneous assay, the extent of complex formation can be measured without a phase separation step.

BRIEF DESCRIPTION OF THE DRAWINGS

FIG. 1 is a diagram depicting the 63 amino acid polypeptide sequence, (peptides B–N) SEQ ID NO:1 and the various peptide fragments derived therefrom. Peptide A (SEQ ID NO:2) contains an additional phenylalanine at the N-terminus. Note that amino acid position 1 starts at glutamine.

FIG. 2 (Parts A–B) shows bar graphs illustrating the effect on assay background values of deleting the first 20 amino acids from the amino terminal end of the polypeptide.

DETAILED DESCRIPTION OF THE PREFERRED EMBODIMENT

The peptide fragments utilized in the improved assays of the present invention are derived from a polypeptide which exhibits antigen-antibody reaction specificity with sera from patients undergoing convalescence from or are afflicted with NANBH. The nucleic acid sequence of the specific polypeptide has been published in EP 0 363 025 (Arima) and is identified therein (as formulae III within claim 2). Immunoreactivity of the clone was ascertained by immunoscreening techniques after creation of a lambda gtll library. The peptide sequence corresponding to the nucleotide sequence is shown in FIG. 1, Peptide A, hereof, and constitutes a polypeptide of 63 amino acids, having an arginine at the carboxy-terminus and a glutamine at the amino-terminus. In preparing synthetic polypeptides having this sequence, an additional phenylalanine is added at the N-terminus to prevent cyclization of the terminal glutamine, during cleavage of the peptide from the resin.

All peptide fragments derived from the 63 amino acid polypeptide (as well as the full-sized polypeptide control) were synthesized in the amide form on a Milligen-Biosearch 9600 model peptide synthesizer using fluorenylmethoxy carbonyl (FMOC) amino protection scheme and 1-3 diisopropylcarbodiimide coupling chemistry. The amide form of the sequence was adopted because it could be expected to more closely mimic the biologically active analogue than the free acid form. Activated amino acids were coupled to a 2,4-dimethoxy benzhydrylamine resin. Peptide synthesis was monitored by ninhydrin analysis for all amino acids except proline for which an Isatin test was performed. The synthesized peptide was cleaved from the resin by Reagent R, which comprises trifluoroacetic acid, thioanisole, ethanedithiol and anisol in a volumetric ratio of 90:5:3:2.

Peptides cleaved from resins were purified by high performance liquid chromatography (HPLC), and characterized by Porton PI 20 90 E Integrated Micro-Sequencing System to confirm the correct sequence. Purity was ascertained by HPLC on a reverse phase column using a linear gradient in 0.1% trifluoroacetic acid from 5 to 40% acetonitrile over 35 minutes. Absorbance was followed at 230 nm.

Alternatively, recombinant peptides can be produced biologically in clones by manipulation of promoter, ribosome-binding, and translation terminator sites.

The peptides of the present invention may be conveniently used in any assay system utilizing a protein target. In the preferred embodiment, the target peptide fragment is coated onto a solid matrix, such as paramagnetic microparticles, by passive or covalent coating methods. Following an incubation step in the presence of anti-NANBH antibodies, the bound antibody peptide complex is separated from any unreacted antibodies by magnetic separation, and the amount of antibody in the antibody peptide complex is determined.

Conveniently, detection of complexed anti-NANBH antibody can be carried out by further reacting the complex with anti-human antisera to which an enzyme is attached. Upon separation of the tagged complex on paramagnetic particles, by magnetic separation and washing, a fluorescence-producing enzyme substrate is added. The amount of fluorescence measured is thus directly proportional to the amount of anti-NANBH antibody present in the sample.

In an alternative embodiment, the peptides of the present invention may be coated onto microtiter plate wells in the classical enzyme linked immunosorbent assay (ELISA), incubated with sample, aspirated, and an enzyme-conjugated anti-human antisera added. Detection is conventionally carried out by adding the appropriate substrate/chromogen and measuring the resultant product. For a general discussion of ELISA see Langone, et at., Immunological Techniques, Part D Immunoassays. Methods in Enzymology, p. 84 (1982).

Further alternative assay formats which are applicable to the present peptides include Western Blot, Towbin, et al., Proc. Nat. Acad. Sci., 76: 4350 (1979); Radioimmune Assay (RIA), Walsh, et al., J. Infect. Dis., 21: 550 (1970); Competitive Assays, Diamandis, Clin., Biochem., 21: 139 (1988); Noncompetitive Assays, Crook, et al., J. Gen. Virol., 46: 29 (1980); Immunoprecipitation, Tojo, et al., Clin. Chem. 34: 2423 (1988) and Dot Blots, Jahn, et at. Proc. Natl Acad Sci 81: 1684 (1984); PCFIA, Jolley et al, J. Immunol. Meth. 67: 21 (1984).

Of particular interest, is a homogeneous assay based on fluorescence polarization. In this assay, the target peptide fragment is conjugated to a fluorophore, such as fluorescein, and incubated with a sample containing anti-NANBH antibodies to form an antibody peptide complex, followed by measurement of the increased fluorescence polarization. This is an attractive alternative to other assays, in that phase separation steps are unnecessary, and the result can be read directly from the initial reaction mix.

The peptides of the present invention are also useful as vaccines in the treatment of NANBH infection. Since the epitopes of the 63mer polypeptide are all contained in the family of peptide fragments from which the N-terminal nonspecific binding sequence is deleted, the fragments retain all of the antigenic determinants if used as a vaccine. The serial bleed data set forth hereafter suggests that these peptides may define at least one dominant epitope, since detection for many patient sera occurs on earlier bleeds than are detected by the assays currently on the market.

Referring to FIGS. 1, the peptides of the present invention comprise a family of peptides encompassed by the carboxy-43mer peptide of the 63(64)mer (peptide A) described by Arima extending from substantially residue number 63 to about residue 21 at the amino terminal end.

It should be emphasized that minor changes in sequence, e.g. amino acids substitutions, additions or deletions may not appreciably affect assay performance. Thus, peptides having such minor changes in structure are considered the equivalents of peptides having strict homology to the sequence of the original polypeptide.

In FIG. 1, the amino acid sequence of the entire sequence is set out horizontally in a number of vertical rows with lines therebetween indicating the corresponding extent of the individual peptide fragment synthesized according to the above generalized, protocol. Thus, for example the second such line in FIG. 1 projecting horizontally, defines the peptide comprising the 12 to 63mer; and the third such line projecting horizontally, defines the peptide comprising the 21 to 63mer inclusive, and so forth.

The peptides of the present invention were utilized as targets in anti-NANBH antibody assays configured either in paramagnetic microparticle or coated well ELISA format, as described above, and as more fully described in the Examples that follow. The results indicate that assay performance improves significantly when the amino-terminal residues are deleted to produce peptide fragments extending from substantially the carboxy-terminal arginine to any residue in the sequence from about residue 26 to 21.

The dramatic improvement in assay performance results from the loss of significant background (nonspecific binding) with concomitant gain in signal.

EXAMPLE 1

Peptides were prepared as indicated above corresponding to the sequences depicted in FIG. 1. Peptides were then passively coated onto paramagnetic microparticles (0.1–10 microns in size) according to the following procedure: 250 ul of 5% weight/volume 4.0 um paramagnetic particles were pelleted in microfuge at 5000 rpm for 5 minutes. The supernatant was removed and the particle pellet resuspended with 500 ul of 70% ethanol for 15 minutes. The particles were then pelleted as before and supernatant removed. The particles were resuspended in 500 ul of 0.1M CAPS buffer ((3-Cyclohexyamino)-1-propane sulfonic acid) at pH=11.0. The particles were pelleted as before and supernatant removed.

Lyophilized peptide was weighed out and resuspended in sterile filtered (0.22 u) water, resulting in a peptide concentration of 10 mg/mL and allowed to dissolve into solution for 30 minutes at room temperature. The dissolved peptide was further diluted to 500 ug/mL in 0.1M CAPS buffer at pH=11.0 and allowed to stabilize for 20 minutes at room temperature. 250 ul of this peptide solution was then transferred to the washed particle pellet. The particles were resuspended and then tumbled for 12 to 16 hours at room temperature.

The passively absorbed peptide particles were then pelleted at 5000 rpm for 3.5 minutes, supernatant removed and particles resuspended two times in isotonic buffered saline with 0.05% Tween 20 detergent. The particles were further pelleted and resuspended three times in isotonic buffered saline. The coated particles are then resuspended in isotonic buffered saline at final particle concentration of 0.025% weight to volume.

EXAMPLE 2

A paramagnetic particle assay using particles coated with peptide fragments described in FIG. 1 was performed as follows: Human serum or plasma was diluted 1:100 in well buffer (0.103M Tris-HCl, pH 7.4, 1.05M Sodium Chloride, 0.33% NP-40, 0.09% Sodium Azide, and 15% Newborn Calf Serum).

50 ul of the diluted sample was added to each well of a Pandex black microtiter plate. Samples were tested in replicates of at least 2. Paramagnetic particles, coated with peptides as described in Example 1, were added to each well (20 ul). The plate was then placed at 37° C. for 30 minutes.

Upon completion of the incubation, the particles in the wells were washed with 100 ul PBS and Tween-20 (2.06 g sodium phosphate dibasic, 0.318 g sodium phosphate monobasic, 0.5 ml Tween-20, 8.76 g sodium chloride, and 1.0 g sodium azide per liter; pH 7.4). During the wash steps, the paramagnetic particles were held in the microfilter plate well via a magnetic field applied to the bottom of the plate. Particles were washed in this manner five times.

Particles in each well were resuspended in 30 ul of Particle Resuspension Buffer (4.346 g sodium phosphate dibasic, 0.524 g sodium phosphate monobasic, 8.76 g sodium chloride, and 1 g sodium azide per liter; pH 7.4). 20 ul of goat anti-human IgG (H+L) conjugated with B-galactosidase (conjugate) and diluted 1:1,000 in conjugate dilution buffer (0.1M Tris-HCl pH 7.5, 0.5M Sodium chloride, 5% glycerol, 2.3 mM magnesium chloride, 0.1% sodium azide and 20% newborn calf sera) was then added to the wells.

Any human IgG or IgM that was bound to the particles was recognized by and associated with conjugate. The conjugate solution was designed to give maximum liquid stability and reactivity. In particular, newborn calf serum is preferred over calf serum. After incubation with conjugate for 15 minutes at 37° C. the particles in the wells were washed five times with PBS and Tween-20 as described above to remove essentially all of the unbound conjugate. The Tween-20 in the wash solution enhanced the washing process and removed nonspecifically bound conjugate.

Finally, 50 ul of a substrate solution of 4-methyl-umbelliferyl-B-D-galactoside (MUG) was added to each well (0.178 g 4-methyl-umbelliferyl-B-D-galactopyranoside, 3.58 g tricine, 5.1 ml dimethyl sulfoxide, 30 ml methyl alcohol, 0.20 g sodium azide, 0.5 ml Tween-20, per liter, pH 8.5). The presence of B-galactosidase (ie:conjugate) in the wells triggered the cleavage of MUG to generate a fluorescent coumarin product. This reagent and conjugate were used as a sensitive detection system. Fluorescence (excitation wavelength 400 nm/emission wavelength 450 nm) was measured at two timed intervals (i.e. 2 and 14 minutes) post MUG addition. The difference between the two values was a kinetic measurement of fluorescent product generation and is a direct measurement of conjugate and human IgG/IgM bound to the particles. Fluorescent values were converted to nM coumarin values using various concentrations of coumarin itself and its resultant fluorescence to establish a standard curve.

EXAMPLE 3

A paramagnetic particle assay using NANBH sera and normal donor sera was performed as described in Example 2. Table 1A is a summary of results comparing the performance of peptide fragments B, C, D, E, F & G (as detailed in FIG. 1).

The results for the reactivity of four NANBH patient sera are represented as signal to noise and were determined by the following calculation: NANBH positive specimen fluorescence divided by the average fluorescence of three different normal specimens.

Table 1B presents the number of standard deviations (obtained from 3 normal samples) that a particular positive sample lies from the mean of the 3 normal samples. Both sets of data demonstrate that fragment C yields the best assay performance in that the highest signal to noise ratio is obtained and in addition results in the largest number of standard deviations a positive lies from negatives.

EXAMPLE 4

The experiment presented graphically in FIG. 2 compares the performance of Peptide A, (FIG. 2A) the full length sequence, with that of peptide fragment C (FIG. 2B) using the paramagnetic particle assay as described in Example 2. Thirteen samples are plotted on the X-axis and their respective assay fluorescence values (nM coumarin) plotted on the Y-axis.

Sample number 1 is from a NANBH individual,

Sample number 2–12 are from normal donors and sample 13 is a sample dilution buffer control.

The data demonstrates that removing 20 amino acids (1–20) from the amino terminal end of the peptide does not reduce NANBH specimen reactivity but does dramatically reduce non-specific binding reactivity (background) of negative sera.

EXAMPLE 5

The paramagnetic particle assay was performed according to Example 2 using peptide fragments A, B, and C coated separately onto particles. Plasma from ten different NANBH individuals and 1 normal donor were tested and the results are presented as signal to noise in Table 2. Signal to noise was calculated as detailed earlier (Example 3).

The data clearly demonstrate that removing 11 amino acids (1–11) from the amino terminal end of the peptide (Peptide B) results in increased discrimination between positive NANBH patient plasma samples and normal plasma samples without loss of reactivity for any positive sample as compared to the full peptide (peptide A).

Removing even more amino acids to produce fragment C (i.e.: 20 amino acids) results in even better assay discrimination.

EXAMPLE 6

In order to further define the N terminal amino acids of fragment A that contribute to background and positive signal the paramagnetic particle assay described in Example 2 was performed with peptide fragments H–L. The peptides were as follows:

- 22 amino acids removed from the amino terminal end of peptide A (Peptide H)
- 23 amino acids removed from the amino terminal end of peptide A (Peptide I)
- 25 amino acids removed from the amino terminal end of peptide A (Peptide J)
- 28 amino acids removed from the amino terminal end of peptide A (Peptide K)
- 30 amino acids removed from the amino terminal end of peptide A (Peptide L)

The results of this experiment are presented in Table 3 as signal to noise of 8 different positive NANBH plasma divided by the mean of 11 normal donor plasma.

Peptides H, I and J show strong nearly equivalent performance. Peptides K and L show dramatically reduced reactivity with 5 of the 8 positive sera and partially reduced reactivity with the remaining 3 positive sera. The reduced signal to noise was due to a loss of positive signal and not due to increased reactivity with normal donors (ie: background). This clearly defines a region within these peptides that contributes to NANBH plasma immunoreactivity. Furthermore, these data indicate that an immunoreactive region exists between amino acids 23–29 and in particular amino acids 26–29, in that removing this region (ie: as in fragment K) diminished positive signal is noted.

EXAMPLE 7

Table 4 compares the performance of peptide A to all of the peptide fragments that have amino acids removed from the amino terminal end (Peptide Fragments B, C, H, I, J, K, & L). In addition, peptide M which comprises Amino acids #9 through #45 was tested as well using the paramagnetic particle assay of Example 2.

The performance of each peptide was determined using the number of standard deviations each positive sample lies from the mean of negative samples and was calculated as described in Table 4.

The data demonstrate that as amino acids are removed from the amino terminus of fragment A assay performance improves in that B is better than A, C is better than B, and H is better than C. Overall assay performance was comparable for H, I and J. Fragments K, L and M have poor assay performance which was due to diminished NANBH positive signal reactivity. Fragment M contains the immunoreactive region between amino acids 23 and 29 as described in Example 6, yet demonstrates poor reactivity to positive samples. Fragment M does not contain the 7 carboxy terminus amino acids of fragments A, B, C, H, I, J, K or L, thus, these carboxy terminus amino acids in combination with amino acids 23 to 29 are required for NANBH positive sample reaction and good assay performance.

EXAMPLE 8

The data presented in Table 5 demonstrates the effect of removing 7 amino acids from the carboxy terminal end of Peptide fragment H resulting in fragment N. The results were obtained with the paramagnetic particle assay described in Example 2 and are presented as signal to noise values.

A dramatic reduction in signal to noise with NANBH plasma samples number 2, 5 and 6 clearly demonstrates that specific amino acid residues within amino acid numbers 56–63 must be included in a fragment to achieve the best assay performance.

EXAMPLE 9

The peptide fragments described in FIG. 1 were tested using an ELISA coated well microtiter plate format. The assay was performed as follows: Peptide A was diluted to 75 ug/ml in 0.1 M CAPS buffer, pH 11.0 and 50 ul of this solution was added to appropriately marked wells (48 wells of a Costar 96 Well EIA Plate) and the peptide was allowed to adsorb overnight at room temperature. Similarly in the remaining 48 wells 50 ul of fragment H solution was pipetted and allowed to absorb.

The wells were washed 5 times with 100 ul of phosphate buffered saline (PBS) with 0.05% Tween-20 and 5 additional times with 100 ul PBS. The coated plate was then tested using a standard microtiter plate assay format. Conjugate, wash buffer and substrate were from an Ortho ELISA test system.

200 ul of specimen diluent was added to each well then 20 ul of each specimen (serum or plasma) was added to the well. The plate was gently mixed for 10 seconds then placed at 37° C. for 1 hr. The plate was washed 5 times with PBS-Tween then 200 ul anti-human Ig horseradish peroxidase conjugate was added to all wells and incubated for 1 hr. at 37° C. The wells were then washed as before and 200 ul of OPD (O-phenylenediamine-2HCl)/substrate was added to each well. After 30 minutes at room temperature in the dark, 50 ul 4N Sulfuric acid was added to each well. Optical Density was determined at 490 nm in a Biotek plate reader.

The results in Table 6A and 6B compare the reactivity of Peptide A to Peptide H using nine NANBH patient sera and twelve normal sera. As seen with the paramagnetic particle assay, the ELISA system utilizing the improved peptide fragment (fragment H) shows increased performance levels for the discrimination of positive NANBH patient sera from that of normal patient sera. Table 6A presents the results as Signal to noise and Table 6B presents the results as the number of standard deviations a positive NANBH patient sera lies from a negative (normal) population mean.

EXAMPLE 10

Plasma from a succession of six sequential bleeds of two patients having NANBH infections were assayed using fragment H and the paramagnetic particle assay described in Example 2. The data summarized in Table 7 indicates that peptides of the present invention are capable of detecting positive specimen reactions at similar or earlier bleed dates compared to a commercial (Ortho HCV ELISA Test System) test manufactured by Ortho Diagnostics Inc.

TABLE 1A

Reactivity of NANBH Plasma Specimens to Peptide Fragments*

| NANBH Sample | FRAGMENT | | | | | |
|---|---|---|---|---|---|---|
| | B | C | D | E | F | G |
| 1 | 6.7 | 42.8 | 1.4 | 2.9 | 0.1 | 0.3 |
| 2 | 12.7 | 79.9 | 0.6 | 2.8 | 0.1 | 0.2 |
| 3 | 7.7 | 46.1 | 2.1 | 0.5 | 0.2 | 54.6 |
| 4 | 1.3 | 10.3 | 1.4 | 1.2 | 0.1 | 6.1 |

*Results represent signal to noise (background), determined as follows:
Positive specimen fluorescence divided by average fluorescence of 3 different normal specimens
NOTE:
Signal to Noise ratio >1.0 indicates peptide sequence reacts with NANBH positive patient plasma more so than with NANBH negative patient plasma

TABLE 1B

Number of Standard Deviations Distancing Positive NANBH Plasma Specimen Reactivity From Normal (Negative) Plasma Specimen Reactivity*

| NANBH Sample | FRAGMENT | | | | | |
|---|---|---|---|---|---|---|
| | B | C | D | E | F | G |
| 1 | 9 | 58 | 3 | 0 | 0 | 0 |
| 2 | 19 | 109 | 0 | 0 | 0 | 0 |
| 3 | 11 | 63 | 7 | 0 | 0 | 83 |
| 4 | 0 | 13 | 3 | 0 | 0 | 8 |

*Results represent Number of Standard Deviations a Sample is away from negative mean and are calculated as follows: (Positive NANBH Sample Value - Average Values of 3 Negative Samples) divided by the Standard Deviation of Average Value of the 3 Negative Samples.

TABLE 2

Signal to Noise Comparison of Peptide Fragments*

| POSITIVE NANBH Sample | FRAGMENT | | |
|---|---|---|---|
| | A | B | C |
| 1 | 37 | 86 | 110 |
| 2 | 38 | 112 | 112 |
| 3 | 19 | 35 | 37 |
| 4 | 4 | 11 | 12 |
| 5 | 2 | 4 | 4 |
| 6 | 134 | 203 | 242 |
| 7 | 22 | 38 | 39 |
| 8 | 5 | 20 | 18 |
| 9 | 24 | 23 | 26 |
| 10 | 24 | 77 | 91 |

*Results represent signal to noise (background) determined as follows:
Positive specimen fluorescence divided by the fluorescence of a negative specimen.
Signal to Noise ratio >1.0 indicates peptide sequence reacts with NANBH positive patient sera more so than with NANBH negative patient sera.

TABLE 3

Reactivity of NANBH Plasma Specimens to Peptide Fragments*

| POSITIVE NANBH Sample | FRAGMENT | | | | |
|---|---|---|---|---|---|
| | H | I | J | K | L |
| 1 | 5.4 | 5.3 | 4.7 | 0.3 | 0.8 |
| 2 | 110.0 | 140.5 | 102.4 | 0.2 | 0.6 |
| 3 | 18.8 | 20.8 | 27.1 | 15.3 | 16.8 |
| 4 | 32.4 | 29.7 | 25.3 | 0.1 | 0.3 |
| 5 | 75.0 | 92.0 | 89.7 | 0.3 | 0.4 |
| 6 | 15.5 | 15.5 | 13.5 | 8.4 | 2.5 |
| 7 | 40.3 | 39.9 | 32.7 | 20.9 | 4.8 |
| 8 | 33.2 | 25.5 | 20.1 | 0.6 | 1.7 |

*Results represent signal to noise (background), determined as follows:
Positive specimen fluorescence divided by average fluorescence of 11 different negative specimens.
Signal to Noise ratio >1.0 indicates peptide sequence reacts with NANBH positive patient sera more so than with NANBH negative patient sera.

TABLE 4

Number of Standard Deviations Distancing Positive NANBH Plasma Specimen Reactivity From Normal (Negative) Plasma Specimen Reactivity*

| NANBH Sample | FRAGMENT | | | | | | | |
|---|---|---|---|---|---|---|---|---|
| | A | B | C | H | I | J | K | L | M |
| 1 | 0 | 0 | 2 | 5 | 5 | 5 | 0 | 0 | 0 |
| 2 | 9 | 21 | 76 | 108 | 144 | 125 | 0 | 0 | 8 |
| 3 | 3 | 3 | 14 | 18 | 21 | 32 | 12 | 51 | 5 |
| 4 | 2 | 5 | 14 | 31 | 30 | 30 | 0 | 0 | 0 |
| 5 | 7 | 13 | 41 | 73 | 94 | 109 | 0 | 0 | 3 |
| 6 | 0 | 3 | 9 | 14 | 15 | 15 | 6 | 5 | 4 |
| 7 | 3 | 7 | 23 | 39 | 40 | 39 | 16 | 12 | 8 |
| 8 | 1 | 4 | 11 | 32 | 25 | 24 | 0 | 2 | 2 |

*Results represent Number Standard Deviations a Sample is away from negative mean and are calculated as follows: (Sample Value - Average Values 11 Negative Samples) divided by the Standard Deviation of Average Value of the 11 Negative Samples.

TABLE 5

Effect of Removing 8 Amino Acids from the C terminus*

| POSITIVE NANBH Sample | FRAGMENT | |
|---|---|---|
| | H | N |
| 1 | 4 | 2 |
| 2 | 78 | 42 |
| 3 | 26 | 23 |
| 4 | 26 | 25 |
| 5 | 160 | 41 |
| 6 | 99 | 47 |
| 7 | 13 | 10 |
| 8 | 32 | 23 |
| 9 | 15 | 6 |

*Results represent signal to noise (background), determined as follows:
Positive specimen fluorescence divided by average fluorescence value of 11 different negative specimen.
Signal to Noise ratio >1.0 indicates peptide sequence reacts with NANBH positive patient sera more so than with NANBH negative patient sera.

TABLE 6A

Coated Well EIA: Peptide Fragment Comparison
Signal to Noise Comparison of Peptide Fragments*

| NANBH Sample | FRAGMENT A | FRAGMENT H |
|---|---|---|
| 1 | 1.2 | 6.0 |
| 2 | 1.5 | 51.1 |
| 3 | 17.2 | 63.7 |
| 4 | 16.8 | 61.4 |
| 5 | 19.6 | 55.2 |
| 6 | 8.6 | 31.2 |
| 7 | 7.5 | 19.1 |
| 8 | 10.9 | 27.8 |
| 9 | 10.2 | 41.8 |

*Results represent signal to noise (background), determined as follows:
Positive specimen O.D. divided by the average O.D. of 12 different negative specimen.
Signal to Noise ratio >1.0 indicates peptide sequence reacts with NANBH positive patient sera more so than with NANBH negative patient sera.

TABLE 6B

Coated Well EIA Assay: Peptide Fragment Comparison
Number of Standard Deviations Distancing Positive
NANBH Plasma Specimen Reactivity From Normal
(Negative) Plasma Specimen Reactivity*

| NANBH Sample | FRAGMENT A | FRAGMENT H |
|---|---|---|
| 1 | 0.16 | 3.62 |
| 2 | 0.42 | 48.7 |
| 3 | 16.1 | 61.34 |
| 4 | 15.74 | 58.97 |
| 5 | 18.51 | 52.78 |
| 6 | 7.53 | 28.85 |
| 7 | 6.45 | 16.75 |
| 8 | 9.79 | 25.42 |
| 9 | 9.12 | 39.42 |

*Results represent Number Standard Deviations a Sample is away from negative mean and are calculated as follows:

TABLE 6B-continued

Coated Well EIA Assay: Peptide Fragment Comparison
Number of Standard Deviations Distancing Positive
NANBH Plasma Specimen Reactivity From Normal
(Negative) Plasma Specimen Reactivity*

| NANBH Sample | FRAGMENT A | FRAGMENT H |
|---|---|---|

(Positive NANBH Sample Value - Average Values 12 Negative Samples) divided by the Standard Deviation of Average Value of the 12 Negative Samples.

TABLE 7

Comparison of Fragment H Assay Performance - VS.
ORTHO HCV ELISA Using Commercial HCV Serial Bleed Panels

| Bleed Date: | FRAGMENT H Signal/Noise* | Ortho HCV ELISA Signal/Cutoff** |
|---|---|---|
| Donor A | | |
| 07/28/88 | 0.2 | 0.1 |
| 08/22/88 | 0.2 | 0.1 |
| 09/08/88 | 0.2 | 0.1 |
| 09/28/88 | 49.9 | 3.8 |
| 12/12/89 | 73.3 | 6.0 |
| 01/13/89 | 52.3 | 6.0 |
| Donor B | | |
| 07/19/88 | 21.3 | 0.1 |
| 08/19/88 | 9.2 | 0.1 |
| 08/30/88 | 11.4 | 0.1 |
| 09/28/88 | 29.7 | 0.5 |
| 11/09/88 | 28.7 | 6.0 |
| 03/17/89 | 174.6 | 6.0 |

*Signal/Noise is determined as follows: Positive specimen fluorescence divided by negative specimen fluorescence.
**Signal/Cutoff is determined as follows: Positive specimen O.D. divided by calculated cutoff O.D.

We claim:

1. In an assay for diagnosing NANBH utilizing a polypeptide having substantially the amino acid sequence QEKK-GEASNGEAENDTHKKQRRYKEKEKTAT-NNPGKNKKPRVGRIKNWNREGRKDAyQIR KRR SEQ ID NO:1 and containing at least one epitope reactive to NANBH positive sera, the improvement consisting of a target peptide fragment thereof extending from an amino acid residue corresponding to any one of residues 21 to 26 from the amino end of the polypeptide to at least the amino acid residue corresponding to residue 56 from the amino end of the polypeptide wherein the sensitivity of the assay to NANBH positive samples utilizing the peptide fragment is greater than the sensitivity of the assay to NANBH positive samples utilizing the entire polypeptide.

2. The improved assay of claim 1 wherein the target peptide fragment is coated onto a solid matrix, and the assay is carried out by incubating with a sample containing antibodies directed to the peptide fragment to form an antibody peptide complex, separating unreacted antibodies from the complex immobilized onto said solid matrix, and quantitating the amount of antibody in said complex with detecting means.

3. The improved assay of claim 1 wherein the target peptide fragment is conjugated to a fluorophore, and the assay is carried out by incubating with a sample containing antibodies to said peptide to form an antibody peptide complex, and measuring the fluorescence polarization of the complex.

4. The assay of claim 2 wherein the solid matrix comprises particles of size range of about 0.1 to 100 um.

5. The assay of claim 2 wherein solid matrix is a microtiter plate.

6. The assay of claim 2 wherein the solid matrix is polystyrene or carboxyl or amino functionalized paramagnetic particles for passive and/or covalent coupling.

7. The particles of claim 4 wherein said particles are paramagnetic.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 63 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:1:

```
Gln Glu Lys Lys Gly Glu Ala Ser Asn Gly Glu Ala Glu Asn Asp Thr
 1               5                  10                  15

His Lys Lys Gln Arg Arg Tyr Lys Glu Lys Glu Lys Thr Ala Thr Asn
                20                  25                  30
```

```
         Asn  Pro  Gly  Lys  Asn  Lys  Lys  Pro  Arg  Val  Gly  Arg  Ile  Lys  Asn  Trp
                   3 5                      4 0                      4 5

Asn  Arg  Glu  Gly  Arg  Lys  Asp  Ala  Tyr  Gln  Ile  Arg  Lys  Arg  Arg
              5 0                      5 5                 6 0
```

( 2 ) INFORMATION FOR SEQ ID NO:2:

( i ) SEQUENCE CHARACTERISTICS:
        ( A ) LENGTH: 64 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:2:

```
         Phe  Gln  Glu  Lys  Lys  Gly  Glu  Ala  Ser  Asn  Gly  Glu  Ala  Glu  Asn  Asp
         1              5                        1 0                           1 5

Thr  His  Lys  Lys  Gln  Arg  Arg  Tyr  Lys  Glu  Lys  Glu  Lys  Thr  Ala  Thr
                   2 0                           2 5                      3 0

Asn  Asn  Pro  Gly  Lys  Asn  Lys  Lys  Pro  Arg  Val  Gly  Arg  Ile  Lys  Asn
                        3 5                      4 0                      4 5

Trp  Asn  Arg  Glu  Gly  Arg  Lys  Asp  Ala  Tyr  Gln  Ile  Arg  Lys  Arg  Arg
              5 0                      5 5                 6 0
```